United States Patent [19]

Inoue et al.

[11] 4,119,512
[45] Oct. 10, 1978

[54] AIR-FUEL RATIO DETECTING APPARATUS

[75] Inventors: Tokuta Inoue, Mishima; Takehisa Yaegashi; Keiji Aoki, both of Susono, all of Japan

[73] Assignee: Toyota Jidosha Kogyo Kabushiki Kaisha, Toyota, Japan

[21] Appl. No.: 756,286

[22] Filed: Jan. 3, 1977

[30] Foreign Application Priority Data

Feb. 9, 1976 [JP] Japan .................................. 51-12338

[51] Int. Cl.² ............................................ G01N 27/46
[52] U.S. Cl. .............................. 204/195 S; 123/119 E
[58] Field of Search ............................ 204/15, 195 S; 123/119 E

[56] References Cited

U.S. PATENT DOCUMENTS

| | | | |
|---|---|---|---|
| 2,955,999 | 10/1960 | Tirrell | 204/290 F |
| 3,096,272 | 7/1963 | Beer | 204/290 F |
| 3,347,767 | 10/1967 | Hickam | 204/195 S |
| 3,935,089 | 1/1976 | Togawa et al. | 204/195 S |
| 4,021,326 | 5/1977 | Pollner et al. | 204/195 S |

FOREIGN PATENT DOCUMENTS 2,454,339  5/1975  Fed. Rep. of Germany ....... 204/195 S

*Primary Examiner*—T. Tung
*Attorney, Agent, or Firm*—Stevens, Davis, Miller & Mosher

[57] ABSTRACT

An electrode structure for air-fuel ratio detecting, including a grate-like or perforated metal plate coated with a layer of alumina which is coated with a layer of platinum which is in electrical contact with a solid electrolyte which is formed for contacting both exhaust gases and the ambient atmosphere, so that when the platinum is exposed to engine exhaust gases catalytic action of the platinum lowers the oxygen partial pressure at the electrolyte surface to its equilibrium concentration causing an abrupt change in electromotive force detectible between a positive electrode in electrical contact with the solid electrolyte, and the grate electrode.

10 Claims, 6 Drawing Figures

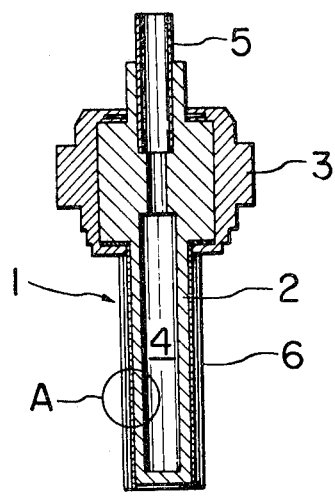
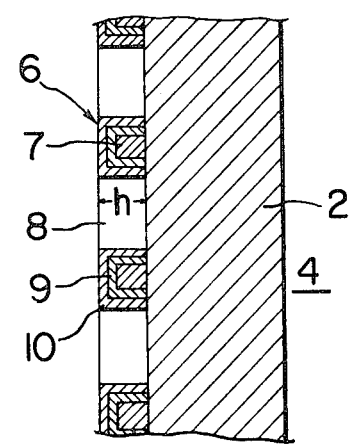
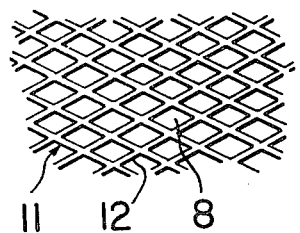

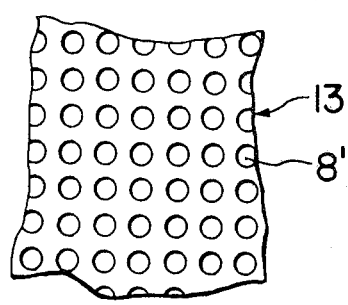
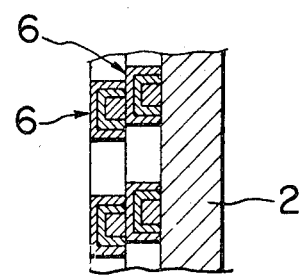
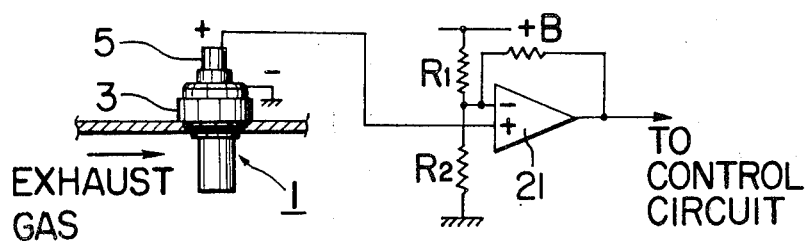

AIR-FUEL RATIO DETECTING APPARATUS

BACKGROUND OF THE INVENTION

This invention relates to an air-fuel ratio detecting apparatus which detects the air-fuel ratio of the intake mixture sucked into an engine from time to time by sensing the oxygen concentration of its exhaust gas.

Among various means proposed for eliminating noxious exhaust pollutants such as hydrocarbons, and oxides or carbon and nitrogen (HC, CO and $NO_x$) is a three way catalytic converter which can eliminate HC, CO and $NO_x$ at the same time. For the simultaneous treatment of these three noxious combustion products, the three way catalytic converter necessitates exact control of the intake mixture to the stoichiometone air-fuel ratio, which in turn requires an accurate air-fuel ratio control system.

There is a known air-fuel ratio detecting apparatus taking advantage of the known fact that electromotive force is produced if an oxygen partial pressure exists between two electrodes in an electrolyte having oxygen ions. Based on the principle that oxygen concentration in exhaust gas changes with the intake air-fuel ratio, this air-fuel ratio detecting apparatus uses a solid electrolyte and keeps one electrode exposed to the atmosphere and the other electrode in contact with the exhaust gas. Usually platinum is used as the electrodes. The catalytic action of platinum lowers the oxygen partial pressure at the electrolyte surface substantially to the equilibrium concentration, as a result of which electromotive force changes abruptly in the vicinity of the theoretical air-fuel ratio.

The known air-fuel ratio detecting apparatus of the above-described type have had several shortcomings. For instance, phosphorous and lead (P and Pb) in exhaust gases adhere to platinum to ruin its catalytic activity. Impingement of small iron pieces and other fine grains floating in exhaust gases scratches off the electrolyte or causes separation of the electrodes, which leads to malfunction of the detecting apparatus.

BRIEF SUMMARY OF THE INVENTION

The object of this invention is to provide an air-fuel ratio detecting apparatus with increased durability and reliability, improving the aforesaid defects.

The feature of this invention lies in that a grate-like or perforated metal plate is formed into an electrode to enclose an electrolyte, and a conductive metal plate coated with a layer of alumina which, in turn, is coated with a layer of platinum, is used as that metal plate.

BRIEF DESCRIPTION OF THE DRAWINGS

Now preferred embodiments of this invention will be described by reference to the accompanying drawings, in which:

FIG. 1 is a cross-sectional view of an air-fuel ratio detecting apparatus embodying this invention.

FIG. 2 is a cross-sectional view enlarging part A of FIG. 1.

FIG. 3 is an exploded view showing an embodiment of the electrode plate.

FIG. 4 is an exploded view showing another embodiment of the electrode plate.

FIG. 5 is a cross-sectional view of an embodiment wherein the electrode plate is wound double.

FIG. 6 is an electrical circuit to which the air-fuel ratio detecting apparatus of this invention may be connected.

DETAILED DESCRIPTION OF THE INVENTION

In FIG. 1, an air-fuel ratio detecting apparatus 1 comprises a solid electrolyte 2 held in a holder 3. The solid electrolyte 2 has a cavity or bore 4 into which the atmosphere is introduced and is made of $ZrO_2$ (zirconium dioxide) possibly with a small percentage of impurities. A cylindrical positive electrode 5 is provided at the inlet through which the atmosphere is introduced, while a negative electrode plate 6, having many small apertures, is provided around the cavity portion 4. Said positive electrode 5 and negative electrode plate 6 are kept in close contact with the solid electrolyte 2.

As will be seen in FIG. 2, the negative electrode plate 6 comprises a conductive metal plate 7 made of platinum having many apertures 8, and on that surface of plate 6 which comes in contact with exhaust gas is formed a layer of alumina 9. On this alumina layer 9 is formed a catalyst layer 10 of noble metal such as platinum.

A grate-like metal plate 11 shown in FIG. 3 is a suitable example of the conductive metal plate 7 with many apertures 8. In this embodiment, the apertures 8 are formed by intersecting ribs 12.

Due to the above-described structure, this invention provides the platinum catalyst layer 10 with increased surface area, but also permits the exhaust gas to uniformly impinge on the entire surface of the electrolyte 2. By appropriately selecting the depth ($h$) of the apertures 8, erosion of the electrolyte 2 by floating particles is reduced, which precludes the separation of the electrode plate 6 from the electrolyte 2.

The alumina layer 9 can be formed by a suitable method, such as metallizing and baking. The formation of the platinum layer 10 over the alumina layer 9 also can be achieved by a suitable known electrochemical, chemical or mechanical method. Electrochemical methods, such as vacuum evaporation methods or ionic beam methods, and chemical methods, such as an electroless plating method can be used to form the platinum layer 10 over the alumina layer 9. Also, any of the methods disclosed in U.S. Pat. Nos. 3,841,987, 3,843,400 and 3,891,529, whose disclosure is incorporated by reference herein, could be used.

It is also contemplated in this invention that the layer 9 could be of $TiO_2$ (titanium dioxide) instead of alumina.

As shown in FIG. 4, an electrode plate provided with many round apertures 8' may also be used.

With respect to shape, the apertures 8 and 8' are not limited to the foregoing embodiments, but can be made in other suitable shapes.

To sufficiently increase the depth of the apertures 8 and 8' to reduce the impinging of the floating particles on the electrode surface and increase the surface area of the platinum catalyst layer, the electrode plate 6 may be wound in a double layer as illustrated in FIG. 5.

The apparatus is used by connecting the bore 4 for communication with the ambient atmosphere, with the exposed catalyst layer 10 and solid electrolyte 2 located in the exhaust gas stream of an engine, and the electrodes connected to any desired electrical metering circuitry or device. As shown in FIG. 6, the output voltage from the air-fuel ratio detecting apparatus is compared at a comparator 21 with a reference voltage, which is determined by division of a constant voltage +B according to the divisional ratio defined by the values of the resistors $R_1$ and $R_2$. The output signal thus obtained from the comparator 21, which corresponds to the voltage difference between the output voltage from the air-fuel ratio detecting apparatus and the reference voltage, is applied to a following control circuit (not shown). Such a circuit is known and is shown for example in FIG. 3 of U.S. Pat. No. 3,815,561, whose disclosure is incorporated by reference herein. The control circuit produces a control signal having a pulse width to define the time interval for the supply of the fuel. The control signal is supplied to a fuel-injecting electromagnetic valve (not shown) whereby the amount of fuel to be supplied is controlled and thus the air-fuel ratio is controlled.

As understood from the foregoing disclosure, this invention offers a highly useful air-fuel ratio detecting apparatus with a simple structure, increased durability and improved detecting ability.

What is claimed is:

1. An air-fuel ratio detecting apparatus for detecting the air-fuel ratio of an internal combustion engine by sensing the composition of exhaust gas from the engine, said apparatus comprising:
   a first electrode;
   a second electrode in the form of a grate having openings defined therein;
   a solid electrolyte which contacts ambient atmosphere near said first electrode and contacts exhaust gas near said second electrode;
   said second electrode being made of substantially solid non-porous materials and comprising:
      an electrically conductive metal material one area of which is in direct electrical and physical contact with the solid electrolyte;
      a first layer of another material convering other areas of the electrically conductive metal than said one; and
      a second layer of a noble metal catalyst covering said first layer; and
   said solid electrolyte is accessible through said openings in said second electrode for direct contact by exhaust gas.

2. The apparatus of claim 1, wherein:
   said electrically conductive metal material is platinum; said first layer is made of alumina; and said second layer is made of platinum.

3. The apparatus of claim 2, wherein:
   the second electrode further comprises:
      an electrically conductive metal material one area of which is in direct electrical and physical contact with said second layer;
      a third layer of material covering other areas of the last-mentioned electrically conductive metal material than said one; and
      a fourth layer of a noble metal catalyst covering said third layer.

4. The apparatus of claim 2, wherein the solid electrolyte has a bore therein for passage of the ambient atmosphere into contact with said solid electrolyte, and said first electrode is in contact with said electrolyte at the surface of said bore, and said second electrode is wrapped around the exterior of said solid electrolyte.

5. The apparatus of claim 1, wherein:
   said electrically conductive metal material is platinum;
   said first layer is made of titanium dioxide; and
   said second layer is made of platinum.

6. The apparatus of claim 5, wherein:
   the second electrode further comprises:
      an electrically conductive metal material one area of which is in direct electrical and physical contact with said second layer;
      a third layer of material covering other areas of the last-mentioned electrically conductive metal material than said one; and
      a fourth layer of a noble metal catalyst covering said third layer.

7. The apparatus of claim 5, wherein the solid electrolyte has a bore therein for passage of the ambient atmosphere into contact with said solid electrolyte, and said first electrode is in contact with said electrolyte at the surface of said bore, and said second electrode is wrapped around the exterior of said solid electrolyte.

8. The apparatus of claim 1, wherein said first electrode is a positive electrode and said second electrode is a negative electrode.

9. The apparatus of claim 1, wherein said solid electrolyte is made of zirconium dioxide.

10. An air-fuel ratio detecting apparatus for detecting the air-fuel ratio of an internal combustion engine by sensing the composition of exhaust gas from the engine, said apparatus comprising:
    a first electrode;
    a second electrode in the form of a grate having openings defined therein;
    a solid electrolyte which contacts ambient atmosphere near said first electrode and contacts exhaust gas near said second electrode;
    said second electrode being made of substantially solid non-porous materials and comprising:
       an electrically conductive metal material the interior surface of which is in direct electrical and physical contact with the exterior surface of the solid electrolyte;
       a first layer of another material covering the remaining surface, other than the interior surface, of the electrically conductive metal material; and
       a second layer of a noble metal catalyst covering said first layer; and
    said solid electrolyte is accessible through said openings in said second electrode for direct contact by exhaust gas.

* * * * *